(12) United States Patent
Baine et al.

(10) Patent No.: US 6,372,933 B1
(45) Date of Patent: Apr. 16, 2002

(54) PROCESS FOR PREPARING CERTAIN PHENYL UREA COMPOUNDS

(75) Inventors: Neil H. Baine, Merion Station; Ann Marie Eldridge, Norristown; Marvin Sungwhan Yu, Audubon, all of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/763,743

(22) PCT Filed: Sep. 26, 1999

(86) PCT No.: PCT/US99/19493

§ 371 Date: Feb. 27, 2001

§ 102(e) Date: Feb. 27, 2001

(87) PCT Pub. No.: WO00/12472

PCT Pub. Date: Mar. 9, 2000

(51) Int. Cl.⁷ .............................................. C07C 255/00

(52) U.S. Cl. ..................... 558/423; 558/411; 564/48; 564/49; 564/50; 564/52; 564/53; 564/55

(58) Field of Search ............................. 564/48, 49, 50, 564/52, 53, 55; 558/411, 423

(56) References Cited

U.S. PATENT DOCUMENTS 4,350,781 A      9/1982   Rasshofer et al.

OTHER PUBLICATIONS

Database CA on STN. AN 96:135731. Domagalina, et al. 1980. "New derivatives of carbamidobenz–oxazoline–2–ones" Ann Univ. Mariae Curie–Sklodowska Sect. D (1980), vol. Date 1979, 35, 121–8, entire abstract.

Primary Examiner—Paul J. Killos
(74) Attorney, Agent, or Firm—Soma G. Simon; William T. King; Charles M. Kinzig

(57) ABSTRACT

This invention relates to a process for making certain phenyl urea compounds by using a Lewis acid to effect the ring opening of a benzoxazolinone by an amine.

8 Claims, No Drawings

PROCESS FOR PREPARING CERTAIN PHENYL UREA COMPOUNDS

SCOPE OF THE INVENTION

This invention relates to a process for making certain phenyl urea compounds. The end-product phenyl urea compounds are useful in treating IL-8, GROα, GROGβ, GROγ and NAP-2 mediated diseases.

BACKGROUND OF THE INVENTION

Interleukin-8 is a chemoattractant for neutrophils, basophils, and a subset of T-cells. It is produced by a majority of nucleated cells including macrophages, fibroblasts, endothelial and epithelial cells exposed to TNF, IL-1a, IL-1b or LPS, and by neutrophils themselves when exposed to LPS or chemotactic factors such as FMLP. M. Baggiolini et al, *J. Clin. Invest.* 84, 1045 (1989); J. Schroder et al, *J. Immunol.* 139, 3474 (1987) and *J. Immunol.* 144, 2223 (1990); Strieter, et al, *Science* 243, 1467 (1989) and *J. Biol. Chem.* 264, 10621 (1989); Cassatella et al, *J. Immunol.* 148, 3216 (1992).

There is a need for treatment in this field, for compounds which are capable of binding to the IL-8 α or β receptor. Therefore, conditions associated with an increase in IL-8 production (which is responsible for chemotaxis of neutrophil and T-cells subsets into the inflammatory site) would benefit by compounds which are inhibitors of IL-8 receptor binding. Such compounds have been disclosed in published patent applications exemplified by the likes of PCT/US96/13632) published Aug. 21, 1997 as WIPO No. WO97/29743.

Specifically this invention provides a method for synthesising N-[2-hydroxy-4-cyanophenyl]-N'-[2-bromophenyl] urea, a compound disclosed in PCT application serial number PCT/US96/13632, published Aug. 21, 1997 an WIPO No. WO97/29743 and related compounds.

SUMMARY OF THE INVENTION

In a first aspect this invention covers a process for making a compound of Formula $$\text{(I)}$$

wherein

X is oxygen;

R is any functional moiety having an ionizable hydrogen and a pKa of 10 or less.

R1 is independently selected from hydrogen; halogen; nitro; cyano; $C_{1-10}$ alkyl; halosubstituted $C_{1-10}$ alkyl; $C_{2-10}$ alkenyl; $C_{1-10}$ alkoxy; halosubstituted $C_{1-10}$alkoxy; azide; $S(O)_tR_4$; $(CR_8R_8)_q S(O)_tR_4$; hydroxy; hydroxy substituted $C_{1-4}$alkyl; aryl; aryl $C_{1-4}$ alkyl; aryl $C_{2-10}$ alkenyl; aryloxy; aryl $C_{1-4}$ alkyloxy; heteroaryl; heteroarylalkyl; heteroaryl $C_{2-10}$ alkenyl; heteroaryl $C_{1-4}$ alkyloxy; heterocyclic, heterocyclic $C_{1-4}$alkyl; heterocyclic$C_{1-4}$alkyloxy; heterocyclic$C_{2-10}$ alkenyl; $(CR_8R_8)_q NR_4R_5$; $(CR_8R_8)_q C(O)NR_4R_5$; $C_{2-10}$ alkenyl $C(O)NR_4R_5$; $(CR_8R_8)_q C(O)NR_4R_{10}$; $S(O)_3H$; $S(O)_3R_8$; $(CR_8R_8)_q C(O)R_{11}$; $C_{1-10}$ alkenyl $C(O)R_{11}$; $C_{2-10}$ alkenyl $C(O)OR_{11}$; $(CR_8R_8)_q C(O)OR_{11}$; $(CR_8R_8)_q OC(O)R_{11}$; $(CR_8R_8)_qNR_4C(O)R_{11}$; $(CR_8R_8)_q C(NR_4)NR_4R_5$; $(CR_8R_8)_q NR_4C(NR_5)R_{11}$, $(CR_8R_8)_q S(O)_2 NR_4R_5$, or two $R_1$ moieties together may form a 5 to 6 membered unsaturated ring, and wherein the alkyl, aryl, arylalkyl, heteroaryl, heterocyclic moieties may be optionally substituted;

q is 0 or an integer having a value of 1 to 10;

t is 0 or an integer having a value of 1 or 2;

s is an integer having a value of 1 to 3;

R4 and $R_5$ are independently, optionally substituted $C_{1-4}$ alkyl, optionally substituted aryl, optionally substituted aryl $C_{1-4}$alkyl, optional v substituted heteroaryl, optionally substituted heteroaryl $C_{1-4}$alkyl, heterocyclic, heterocyclic $C_{1-4}$ alkyl, or $R_4$ and $R_5$ together with the nitrogen to which they are attached form a 5 to 7 member ring which may optionally comprise an additional heteroatom selected from O, N or S;

Y is $R_1$;

q is 0 or an integer having a value of 1 to 10;

m is an integer having a value of 1 to 3;

$R_6$ and $R_7$ are independently hydrogen or a $C_{1-4}$ alkyl group, or $R_6$ and $R_7$ together with the nitrogen to which they are attached form a 5 to 7 member ring which ring, may optionally contain an additional heteroatom which heteroatom is selected from oxygen, nitrogen or sulfur;

$R_8$ is hydrogen or $C_{1-4}$ alkyl;

$R_{10}$ is $C_{1-10}$ alkyl $C(O)_2R_8$;

$R_{11}$ is hydrogen, optionally substituted $C_{1-4}$ alkyl, optionally substituted aryl, optionally substituted aryl $C_{1-4}$alkyl, optionally substituted heteroaryl, optionally substituted heteroaryl$C_{1-4}$alkyl, optionally substituted heterocyclic, or optionally substituted heterocyclic$C_{1-4}$alkyl, $R_{12}$ is hydrogen, $C_{1-10}$ alkyl, optionally substituted aryl or optionally substituted arylalkyl;

$R_{13}$ is suitably $C_{1-4}$ alkyl, aryl, aryl $C_{1-4}$alkyl heteroaryl, heteroaryl$C_{1-4}$alkyl, heterocyclic, or heterocyclic$C_{1-4}$alkyl;

$R_b$ is $NR_6R_7$, alkyl, aryl, aryl $C_{1-4}$ alkyl, aryl $C_{2-4}$ alkenyl, heteroaryl, heteroaryl $C_{1-4}$ alkyl, heteroaryl$C_{2-4}$ alkenyl, heterocyclic, heterocyclic $C_{1-4}$ alkyl, heterocyclic $C_{2-4}$ alkenyl, or camphor, all of which groups may be optionally substituted;

wherein said process comprises reacting a compound of Formula (A)

$$\text{(A)}$$

where $R_1$ is the same as defined in Formula I with a nucleophile illustrated by the amine of Formula (B)

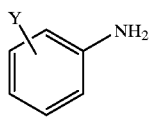

where Y is the same as defined above in the presence of a Lewis acid to open the oxazolinone ring of Formula (A) to form the urea of Formula (I).

In a second aspect, this invention relates to a process for making a compound of Formula (I) as described above wherein the process comprises treating a benzoxazolinone of Formula (D)

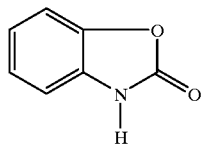

with a halogen in the presence of an acid to form a compound of Formula (C);

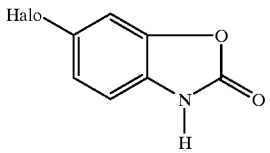

then treating Formula C with CuCN to form a compound of Formula (A1), and

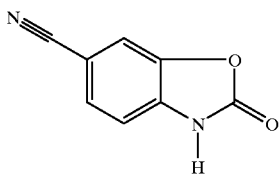

reacting Formula A1 with a nucleophile illustrated by Formula (B)

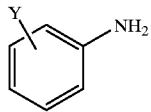

where Y is the same as defined in Formula I in the presence of a Lewis acid to open the oxazolinone ring of Formula (A) and form the compound of Formula (I) where R is OH and $R_1$ is CN.

The preferred compounds which can be synthesised by these methods and using these inter mediates are those where $R_1$ is halogen, cyano, nitro, $CF_3$, $C(O)NR_4R_5$, alkenyl $C(O)NR_4R_5$, $C(O)$ $R_4R_{10}$, alkenyl $C(O)OR_{12}$, heteroaryl, heteroarylalkyl, heteroaryl alkenyl, or $S(O)NR_4R_5$, and preferably one of $R_4$ or $R_5$ is phenyl. A preferred ring substitution for $R_1$ is in the 4-position of the phenyl ring.

Preferably $R_1$ is nitro, halogen, cyano, trifluoromethyl group, or $C(O)NR_4R_5$.

Y is preferably a halogen, $C_{1-4}$ alkoxy, optionally substituted aryl, optionally substituted aryloxy, optionally substituted arylalkoxy, optionally substituted arylalkyloxy, optionally substituted heteroarylalkyloxy, methylenedioxy, $NR_4R_5$. thio$C_{1-4}$alkyl, thioaryl halosubstituted alkoxy, optionally substituted $C_{1-4}$ alkyl, or hydroxy alkyl, Y is more preferably mono-substituted halogen, disubstituted halogen, mono-substituted alkoxy, disubstituted alkoxy, methylenedioxy, aryl, or alkyl, more preferably these groups are mono or di-substituted in the 2'-position or 2'-, 31-position. 25 While Y may be substituted in any of the 5 ring positions, preferably when R is OH, or SH, Y is preferably mono-substituted in the 2'-position or 3'-position, with the 4'-preferably being unsubstituted. If the ring is disubstituted, when R is OH or SH substituents are preferably in the 2' or 3' position of a monocyclic ring. While both $R_1$ and Y can both be hydrogen, it is prefered that at least one of the rings be substituted, preferably both rings are substituted.

Preferred compounds include:

N-[2-hydroxy-4-cyanophenyl]-N'-[2-bromophenyl] urea

N-[2-hydroxy-4-cyanophenyl]-N'-[2,3-dichlorophenyl] urea

N-(2-hydroxy-4-cyanophenyl)-N'-(2-(4-pyridylmethyloxy)phenyl)urea, and

N-(2-hydroxy-4-cyanophenyl)-N'-(2-chlorophenyl)urea.

SPECIFIC EMBODIMENTS OF THE INVENTION

Reaction Scheme 1 details in graphical form the process and representative intermediates which are the subject of this invention.

Scheme 1

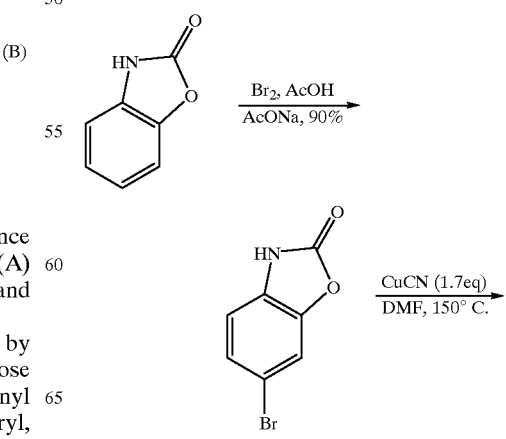

-continued

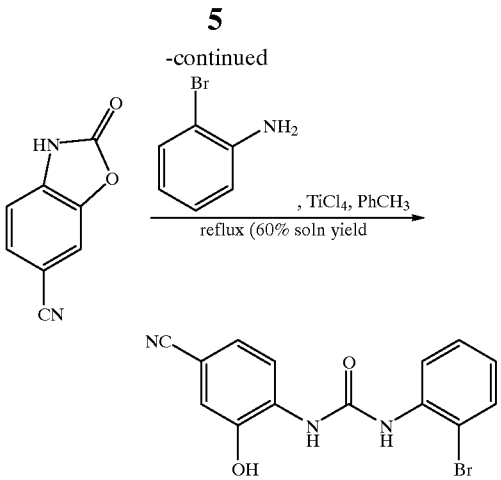

The benzoxazolinone starting material is commercially available (formula 1-1). See for example Aldrich. It is halogenated (formula 1-2) by mixing it with a solution of an organic acid and a the alkali metal salt of that acid in a molar amount about equal to that of the benzoxazolinone and treating that mixture or solution with the halogen. Glacial acetic acid and its sodium salt are the preferred organic acid/salt combination. In the case of the illustrated benzoxazolinone forms. That suspension is cooled to below ambient temperature, somewhere between 0–20° C. and then bromine is added slowly; a slight molar excess of bromine with reference to the benzoxazolinone is preferred. This mixture is stirred at ambient temperature for a period sufficient to effect the reaction, usually about 12 hours to overnight. No special conditions are required to work up the halogenated product.

The nitrile of formula 1-3 is prepared by treating the halogenated benzoxazolinone with CuCN at a moderately elevated temperature under an inert gas in a polar solvent such as dimethyl formamide, N-methyl pyrrolidinone or dimethyl sulfoxide. As illustrated herein, the benzoxazolinone is added to the solvent followed by the CuCN (in about a 75% molar excess). This mixture is heated to a temperature which is in the range of 120–175° C. The reaction is carried out under an inert gas, preferably nitrogen. The reaction mixture is heated to the noted temperature range for about 4–8 hours. Then the reaction is cooled to about 100° C. a 3 to 4-fold molar excess of NaCN is added, and the resulting suspension is stirred for a couple of more hours at ambient temperature. No special workup is required to recover the nitrile.

The urea (formula 1-4) is made by treating the benzoxazolinone with an amine in the presence of a Lewis acid. Exemplary Lewis acids include Ti, Al or Sn (TiCl$_4$, tributyltin chloride, and diethylaluminum). The nitrile of Formula A or A1 is added to a mixture of the salt of the amine and a Lewis acid in a non-polar solvent; 2-bromoaniline is illustrated in Scheme 1. About a 5–7 molar excess of the amine is used and about 2–3 molar excess of the Lew is acid is used. This mixture is refluxed for several hours, for example 5–6 hours. Isolating the product involves cooling the reaction mixture to about 0° C., partitioning with aqueous mineral acid/organic solvent and filtering the organic layer through SiO$_2$.

The following examples are given to illustrate the invention but are not to be taken as limiting what is covered by the claims.

EXAMPLES

Example 1

6-Bromo-2(3H)-benzoxazolone

To a solution of glacial acetic acid (1500 ml) was added sodium acetate (222 g, 2.70 mole) and 2-benzoxazolinone (300 g, 2.22 mole). The suspension was cooled to 15° C. bromine (118 ml, 2.29 mole) added dropwise over 1 h and the mixture stirred for 12 h at ambient temperature. The solids were then filtered, washed with H$_2$O (3×500 ml) and dried under vacuum to give the title compound as a white solid (374 g, 89.7%): mp 186.0–187.0° C.: $^1$H NMR (DMSO-d$_6$) δ 11.8 (s, 1 H), 7.6 (s, 1 H), 7.3 (d, J=8.0 Hz, 1 H), 7.0 (d, J=8.0 Hz, 1 H).

Example 2

2,3-Dihydro-4-hydroxy-2-oxo-6-benzoxazolecarbonitrile

To a solution of DMF (110 ml) was added 6-bromo-2 (3H)-benzoxazolone (50 g, 0.234 mole) and CuCN (89.6 g, 0.398 mole) and the mixture heated to 150° C. for 6 h under nitrogen. The reaction was then cooled to 100° C., H$_2$O (200 ml) and NaCN (36 g, 0.734 mole) added, the suspension stirred for 2 h at ambient temperature and partitioned with EtOAc at 70° C. The organic phase was washed with H$_2$O (2×150 ml) and concentrated in vacuo to give the title compound as a tan solid (33.2 g, 88.5%); mp>220° C.; $^1$H NMR (DMSO-d$_6$) δ 7.8 (s, 1 H), 7.6 (d, J=8.0 Hz, 1 H), 7.2 (d, J=8.0 Hz, 1 H).

Example 3

N-(2-Bromophenyl)-N'-(2-hydroxy-4-cyanophenyl) Urea

A solution of 2-bromoanaline (6.8 g, 39.5 mmol) in toluene (10 mL)/dichloromethane (10 mL) was added to sodium hydride (60%, 1.65 g, 41.0 mmol) and the mixture was warmed to 60° C. for 45 minutes. The mixture was cooled to 5° C. and TiCl$_4$ (1.37 mL, 12.6 mmol) was added over 15 minutes. 2,3-Dihydro-4-hydrozy-2-oxo-6-benzoxazole carbonitrile (1.0 g, 6.0 mmol) was added and the mixture heated at reflux for 5.5 hours. The reaction was cooled to 0° C., partitioned with 15% HCl (25 ml) and EtOAc (150 ml), and the organic phase filtered through SiO$_2$ (50 g). The filtrate was concentrated in vacuo to give a brown solid comprising the title product (0.7 g, 58.6%).

What is claimed is:
1. A process for making a compound of Formula

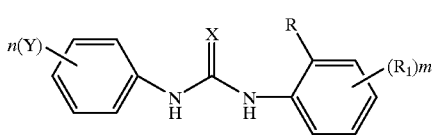

(I)

wherein

X is oxygen;

R is any functional moiety having an ionizable hydrogen and a pKa of 10 or less;

R$_1$ is independently selected from hydrogen; halogen; nitro; cyano; C$_{1-10}$ alkyl; halosubstituted C$_{1-10}$ alkyl; C$_{2-10}$ alkenyl; C$_{1-10}$ alkoxy; halosubstituted C$_{1-10}$ alkoxy; azide; S(O)$_t$R$_4$; (CR$_8$R$_8$)q S(O)$_t$R$_4$; hydroxy; hydroxy substituted C$_{1-4}$ alkyl, aryl; aryl C$_{1-4}$ alkyl; aryl C$_{2-10}$ alkenyl; aryloxy; aryl C$_{1-4}$ alkyloxy; heteroaryl; heteroarylalkyl; heteroaryl C$_{2-10}$ alkenyl; heteroaryl C$_{1-4}$ alkyloxy; heterocyclic, heterocyclic C$_{1-4}$alkyl; heterocyclicC$_{1-4}$alkyloxy; heterocyclicC$_{2-10}$ alkenyl; (CR$_8$R$_8$)q NR$_4$R$_5$; (CR$_8$R$_8$)q C(O)NR$_4$R$_5$;

$C_{2-10}$ alkenyl $C(O)NR_4R_5$; $(CR_8R_8)_q$ $C(O)NR_4R_{10}$; $S(O)_3H$; $S(O)_3R_8$; $(CR_8R_8)_q$ $C(O)R_{11}$; $C_{2-10}$ alkenyl $C(O)R_{11}$; $C_{2-10}$ alkenyl $C(O)OR_{11}$; $(CR_8R_8)_q$ $C(O)$ $OR_{11}$; $(CR_8R_8)_q$ $OC(O)R_{11}$; $(CR_8R_8)_qNR_4C(O)R_{11}$; $(CR_8R_8)_q$ $C(NR_4)NR_4R_5$; $(CR_8R_8)_q$ $NR_4C(NR_5)R_{11}$, $(CR_8R_8)_q$ $S(O)_2NR_4R_5$, or two $R_1$ moieties together may form a 5 to 6 membered unsaturated ring, and wherein the alkyl, aryl, arylalkyl, heteroaryl, heterocyclic moieties may be optionally substituted;

q is 0 or an integer having a value of 1 to 10;

q is 0 or an integer having a value of 1 to 10;

t is 0 or an integer having a value of 1 or 2;

s is an integer having a value of 1 to 3;

$R_4$ and $R_5$ are independently optionally substituted $C_{1-4}$ alkyl, optionally substituted aryl, optionally substituted aryl $C_{1-4}$alkyl, optionally substituted heteroaryl, optionally substituted heteroaryl $C_{1-4}$alkyl, heterocyclic, heterocyclic $C_{1-4}$ alkyl, or $R_4$ and $R_5$ together with the nitrogen to which they are attached form a 5 to 7 member ring which may optionally comprise an additional heteroatom selected from O, N or S;

Y is $R_1$;

q is 0 or an integer having a value of 1 to 10;

m is an integer having a value of 1 to 3;

$R_6$ and $R_7$ are independently hydrogen or a $C_{1-4}$ alkyl group, or $R_6$ and $R_7$ together with the nitrogen to which they are attached form a 5 to 7 member ring which ring may optionally contain an additional heteroatom which heteroatom is selected from oxygen, nitrogen or sulfur;

$R_8$ is hydrogen or $C_{1-4}$ alkyl;

$R_{10}$ is $C_{1-10}$ alkyl $C(O)_2R_8$;

$R_{11}$ is hydrogen, optionally substituted $C_{1-4}$ alkyl, optionally substituted aryl, optionally substituted aryl $C_{1-4}$alkyl, optionally substituted heteroaryl, optionally substituted heteroaryl$C_{1-4}$alkyl, optionally substituted heterocyclic, or optionally substituted heterocyclic$C_{1-4}$alkyl;

$R_{12}$ is hydrogen, $C_{1-10}$ alkyl, optionally substituted aryl or optionally substituted arylalkyl;

$R_{13}$ is suitably $C_{1-4}$ alkyl, aryl, aryl $C_{1-4}$alkyl, heteroaryl, heteroaryl$C_{1-4}$alkyl, heterocyclic, or heterocyclic$C_{1-4}$alkyl;

$R_b$ is $NR_6R_7$, alkyl, aryl, aryl $C_{1-4}$ alkyl, aryl $C_{2-4}$ alkenyl, heteroaryl, heteroaryl $C_{1-4}$ alkyl, heteroaryl$C_{2-4}$ alkenyl, heterocyclic, heterocyclic $C_{1-4}$ alkyl, heterocyclic $C_{2-4}$ alkenyl, or camphor, all of which groups may be optionally substituted;

wherein said process comprises reacting a compound of Formula (A)

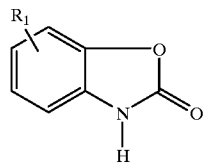

(A)

with a nucleophile illustrated by the amine of Formula (B)

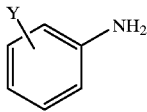

(B)

in the presence of a Lewis acid to open the oxazolinone ring of Formula (A) to form the urea of Formula (I).

2. The process of claim 1 wherein the Lewis acid is $TiCl_4$, tributyltin chloride, or diethylaluminum.

3. The process of claim 1 wherein the product is a compound of Formula I where $R_1$ is halogen, cyano, nitro, $CF_3$, $C(O)NR_4R_5$, alkenyl $C(O)NR_4R_5$, $C(O)$ $R_4R_{10}$, alkenyl $C(O)OR_{12}$, heteroaryl, heteroarylalkyl, heteroaryl alkenyl, or $S(O)NR_4R_5$, and preferably one of $R_4$ or $R_5$ is phenyl;

Y is halogen, $C_{1-4}$ alkoxy, optionally substituted aryl, optionally substituted aryloxy, optionally substituted arylalkoxy, optionally substituted arylalkyloxy, optionally substituted heteroarylalkyloxy, methylenedioxy, $NR_4R_5$, thio$C_{1-4}$alkyl, thioaryl, halosubstituted alkoxy, optionally substituted $C_{1-4}$ alkyl, or hydroxy alkyl; and R is OH.

4. The process of claim 1 wherein Y is halogen.

5. The process of claim 1 wherein $R_1$ is CN.

6. The process of claim 3 where the Lewis acid is $TiCl_4$.

7. The process of claim 6 wherein the product is

N-[2-hydroxy-4-cyanophenyl]-N'-[2-bromophenyl] urea

N-[2-hydroxy-4-cyanophenyl]-N'-[2.3-dichlorophenyl] urea

N-(2-hydroxy-4-cyanophenyl)-N'-(2-(4-pyridylmethyloxy)phenyl)urea, or

N-(2-hydroxy-4-cyanophenyl)-N'-(2-chlorophenyl)urea.

8. A process for making a compound of Formula (I) according to claim 1 wherein the process comprises treating a benzoxazolinone of Formula (D)

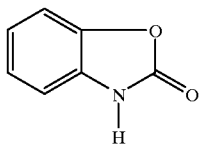

(D)

with a halogen in the presence of an acid to form a compound of Formula (C);

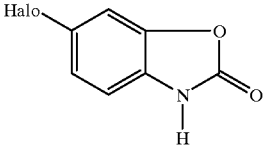

(C)

then treating Formula C with CuCN to form a compound of Formula (A1), and

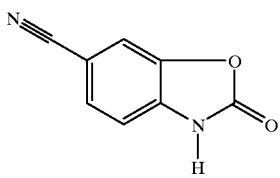

(A1)

reacting Formula (A1) with a nucleophile illustrated by Formula (B)

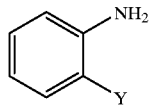

(B)

in the presence of a Lewis acid to open the oxazolinone ring of the compound of Formula (A) and form the compound of Formula (I) where R is OH, $R_1$ is CN and Y is hydrogen; halogen; nitro; cyano; $C_{1-10}$ alkyl; halosubstituted $C_{1-10}$ alkyl; $C_{2-10}$ alkenyl; $C_{1-10}$ alkoxy; halosubstituted $C_{1-10}$ alkoxy; azide; $S(O)_rR_4$; $(CR_8R_8)q\ S(O)_rR_4$; hydroxy; hydroxy substituted $C_{1-4}$alkyl; aryl; aryl $C_{1-4}$ alkyl; aryl $C_{2-10}$ alkenyl; aryloxy; aryl $C_{1-4}$ alkyloxy; heteroaryl; heteroarylalkyl; heteroaryl $C_{2-10}$ alkenyl; heteroaryl $C_{1-4}$ alkyloxy; heterocyclic, heterocyclic $C_{1-4}$alkyl; heterocyclic$C_{1-4}$ alkyloxy; heterocyclic$C_{2-10}$ alkenyl; $(CR_8R_8)q\ NR_4R_5$; $(CR_8R_8)q\ C(O)NR_4R_5$; $C_{2-10}$ alkenyl $C(O)NR_4R_5$; $(CR_8R_8)q\ C(O)NR_4R_{10}$; $S(O)_3H$; $S(O)_3R_8$; $(CR_8R_8)q\ C(O)R_{11}$; $C_{2-10}$ alkenyl $C(O)R_{11}$; $C_{2-10}$ alkenyl $C(O)OR_{11}$; $(CR_8R_8)q\ C(O)OR_{11}$; $(CR_8R_8)q\ OC(O)R_{11}$; $(CR_8R_8)qNR_4C(O)R_{11}$; $(CR_8R_8)q\ C(NR_4)NR_4R_5$; $(CR_8R_8)q\ NR_4C(NR_5)R_{11}$, $(CR_8R_8)q\ S(O)_2NR_4R_5$, or two $R_1$ moieties together may form a 5 to 6 membered unsaturated ring, and wherein the alkyl, aryl, arylalkyl, heteroaryl, heterocyclic moities may be optionally substituted.

* * * * *